United States Patent [19]

Peterson, Jr. et al.

[11] 4,336,395
[45] Jun. 22, 1982

[54] ETHYLENE BRIDGED AMINE FUNCTIONAL SILANES, COMPOSITES USING THE SAME, AND INTERMEDIATES THEREFOR

[75] Inventors: William R. Peterson, Jr., Fallsington; Barry C. Arkles, Oreland, both of Pa.

[73] Assignee: Petrarch Systems, Inc., Levittown, Pa.

[21] Appl. No.: 129,766

[22] Filed: Mar. 12, 1980

[51] Int. Cl.³ .................................................. C07F 7/10
[52] U.S. Cl. ........................................................ 556/413
[58] Field of Search .......................................... 556/413

[56] References Cited

U.S. PATENT DOCUMENTS

| | | | |
|---|---|---|---|
| 3,171,851 | 3/1965 | Pepe | 556/413 |
| 3,247,280 | 4/1966 | Kanner | 556/413 X |
| 3,414,604 | 12/1968 | Pepe et al. | 556/413 X |
| 3,661,963 | 5/1972 | Pepe et al. | 556/413 |

OTHER PUBLICATIONS

Arkles, "Tailoring Surfaces With Silanes", Chemtech 7, pp. 766–778, 12/77.

*Primary Examiner*—Paul F. Shaver
*Attorney, Agent, or Firm*—Seidel, Gonda, Goldhammer & Panitch

[57] ABSTRACT

Ethylene bridged benzylamine trifunctional silanes are provided having the general formula:

$$Z-CH_2-Ph-CH_2CH_2-SiX_3$$

wherein Ph is a phenyl group, at least one X is a hydrolyzable group and Z is a non-hydrolyzable amine functional group. At least one X group is that which is displaced by hydrolysis during the well known reactions of silanes with siliceous substrates, and is preferably methoxy, ethoxy or methoxyethoxy. The Z group is intended to react and bond with polymers in the formation of polymer composites reinforced with siliceous substrates such as glass fibers. The Z group is preferably an amine or alkyl diamine group. The silanes of the invention have excellent thermal stability so that they may be used as coupling agents for composites in which the polymers are processed at temperatures in excess of 350° C. and/or are subject to temperatures in excess of 150° C. for extended periods of time.

7 Claims, No Drawings

ETHYLENE BRIDGED AMINE FUNCTIONAL SILANES, COMPOSITES USING THE SAME, AND INTERMEDIATES THEREFOR

BACKGROUND OF THE INVENTION

The present invention is directed to novel amine functional silanes having improved thermal stability for use in filled polymer composites, and intermediates for producing certain of the novel silanes. More paticularly, the invention relates to ethylene bridged benzylamine derivatives and their use in improving the mechanical properties of polymer composites which are processed at high temperatures or are continuously exposed to high temperatures.

Commercially available silanes, which are conventionally used as coupling agents for polymers filled or reinforced with glass fibers or the like are aliphatic compounds having an amine functional group. Examples of such compounds are 3-aminopropyltriethoxysilane and 3-[2-aminoethyl(aminopropyl)]trimethoxysilane. While these silanes have demonstrated sufficient thermal stability for use with the most common filled resins, the introduction of resins which process in excess of 350° C. or receive continuous exposure to temperatures in excess of 150° C. has made it desirable to produce silane adhesion promoters with greater thermal stability than the aliphatic amine silanes whose thermal stability is insufficient to withstand the above temperatures.

The general order of thermal stability for organosilane coupling agents is shown below:

| | | |
|---|---|---|
| $Z-CH_2CH_2-SiX_3$ | beta substitution | |
| $Z-CH_2-SiX_3$ | alpha substitution | increases |
| $Z-CH_2CH_2CH_2-SiX_3$ | gamma substitution | |
| $Z-CH_2-Ph-SiX_3$ | aromatic substitution | |

In the above formulas Z is a functional group intended to be reactive with the polymer portion of a composite, and X is a hydrolyzable group, typically alkoxy, which is displaced during the reaction with the substrate portion of a composite. The conventional aliphatic silane coupling agents referred to above are of the gamma substitution type.

It has been demonstrated that silane coupling agents having considerable thermal stability can be prepared when aromatic groups are bound to the silicon. Wholly aromatic compounds such as aminophenyltriethoxysilane have been reported as having excellent adhesion promotion properties in polymer composites. However, aromatic silanes have not been commercially attractive due to the adverse economics associated with the multistep syntheses and low yield production of these aromatic silanes.

Recently, a new class of silanes has been developed which incorporates an aliphatic bridge between the aromatic group and the silicon atom. While the thermal stability of these new silanes is not as great as that of the purely aromatic compounds, the thermal stability is significantly greater than the conventionally used gamma functional silanes. Even though an aliphatic bridge segment is present in these compounds, the thermal stability closely resembles that of the aromatic analogs and is only marginally lower. This is surprising since the ethylene bridge plus the methylene group on the functional side of the phenyl group amounts to the same number of methylene groups as in the aliphatic gamma substituted silanes. Ethylene bridged aromatic silanes previously made include (chloromethyl) phenylethyltrimethoxysilane ($ClCH_2-Ph-CH_2CH_2Si(OCH_3)_3$) and styrylethyltrimethoxysilane ($H_2C=CH-Ph-CH_2CH_2Si(OCH_3)_3$).

BRIEF SUMMARY OF THE INVENTION

The novel compounds of the present invention comprise ethylene bridged benzylamine trifunctional silanes of the general formula:

$$Z-CH_2-Ph-CH_2CH_2-SiX_3$$

wherein Ph is a phenyl group (), at least one X is a hydrolyzable group and Z is a non-hydrolyzable amine functional group. The silane compounds have excellent thermal stability and are useful as coupling agents for polymer-filler composites which are processed at high temperatures, particularly polyamides, polysulfones, polyimides and polyphenylene sulfides. When used in such composites at least one X group is displaceable by hydrolysis during the reaction of the silane with a siliceous substrate (e.g. glass fiber reinforcement), and the Z group will react with and form bonds to the polymer of the composite.

Preferably, the X groups are alkoxy, and the Z group is preferably amine or alkyl diamine, such as aminoethylamino. Novel compounds of the invention include (aminomethyl) phenylethyltrimethoxysilane, [aminoethyl(aminomethyl)]phenylethyltrimethoxysilane, and (aminomethyl) phenylethyldimethylmethoxysilane. Their hydrolysates exhibit a 25% weight loss in air at temperatures above 400° C. according to thermogravimetric analysis after dissolving the silanes in water at 5% concentration and drying for four hours at 120° C.

Novel intermediates and a method for producing (aminomethyl) phenylethyldimethylmethoxysilane are also provided.

DETAILED DESCRIPTION OF PREFERRED EMBODIMENTS

The novel compounds of the present invention may be produced by reaction of vinylbenzylchloride with a trifunctional silane which results in opening of the vinyl double bond to form an ethylene bridge between the phenyl group and the silicon atom. The reaction is catalyzed, for example, by chloroplatinic acid. The resulting (chloromethyl) phenylethyl trifunctional silane may then be substituted with the desired X groups on the silane by reaction with ethanol or methanol or trimethyl or triethyl orthoformate, for example. The amine functional derivatives are prepared by reacting with ammonia or the appropriate amine compound.

The X groups attached to the silicon atom may be virtually any of those conventionally used in silane coupling agents, such as alkoxy, alkoxyether, acyloxy and amine. Halogen is not suitable for the X group since it would react with the Z amine functional group. The most common X groups used in commercial silane coupling agents include methoxy, ethoxy and methoxyethoxy, although other lower alkoxy groups may be suitable.

At least one X group is displaceable by hydrolysis during the reaction of the silane with a siliceous substrate. However, up to two of the X groups may be substituted by alkyl, preferably lower alkyl such as methyl or ethyl, groups which are not hydrolyzable and will not react with Z on the molecule.

As used herein, the term "siliceous" will be understood to include not only silicates, such as glass, but other materials having surface chemistry with siliceous properties, such as aluminates, borates, etc. As is well known in silane chemistry, following hydrolysis a reactive silanol group is formed on the coupling agent, which can condense with other silanol groups, for example those on the surface of siliceous fillers, to form siloxane linkages. Stable condensation products are also formed with other oxides such as those of aluminum, zirconium, tin, titanium and nickel.

The compounds of the present invention are particularly useful in connection with polymer composites containing reinforcement or fillers in the form of glass fibers, glass beads, etc., which may be referred to herein generally as siliceous fillers. Such composites are well known for many purposes, and their applicability to the present invention will be discussed more fully below.

The Z group is a non-hydrolyzable amine functional group which will react with and form bonds to various thermosetting and thermoplastic polymers in the formation of filled polymer composites. The Z group may be virtually any amine, including —$NH_2$ itself, mono- or di- substituted amines and polyamines. The amine derivatives are prepared by reacting the chloromethyl intermediate with the appropriate amine, such as ammonia or ethylene diamine.

The novel compounds of the present invention will now be described in more detail with reference to the following specific, non-limiting examples:

EXAMPLE I (Aminomethyl) phenylethyltrimethoxysilane
$H_2NCH_2$—Ph—$(CH_2)_2Si(OCH_3)_3$ (a) A three neck 3 L. flask was charged with 909 ml of trichlorosilane and 127 ml of vinylbenzylchloride (mixed isomers). The flask was equipped with an addition funnel and a Dewar condensor packed with dry-ice/acetone. The mixture was warmed to reflux and 1 ml of 0.1 M $H_2PtCl_6$ in isopropanol was added. Heating was halted. Within 5 minutes an exotherm was observed indicating initiation of the reaction. An additional 1144 ml of vinylbenzylchloride was added over two hours. Distillation of the mixture yielded 2482 g (96% yield) of (chloromethyl) phenylethyltrichlorosilane, b.p. 111°–2°/1.5, density 1.32.

(b) A three neck 2 L. flask equipped with magnetic stirrer, water-cooled condensor and an addition funnel was charged with 1000 ml of trimethylorthoformate and warmed to 40° C. 652 ml of (chloromethyl) phenylethyltrichlorosilane was added dropwise. When evolution of methylchloride was observed, heating was discontinued. Distillation yielded 738 g of (chloromethyl) phenylethyltrimethoxysilane (96% yield), b.p. 112°–19°/1.5.

(c) 274.8 g of (chloromethyl) phenylethyltrimethoxysilane was dissolved in an equal volume of hexane and charged into a 1 L autoclave. The autoclave was sealed, chilled in dry ice/acetone and evacuated. It was then pressurized with 160 g of ammonia. The autoclave was heated to 85° C. for 24 hours. Distillation yielded 61 g (24% yield) of (aminomethyl) phenylethyltrimethoxysilane, b.p. 84–91/0.2.

A hydrolysate of this compound was prepared by dissolving it in water at 5% concentration. The hydrolysate was dried for four hours at 120° C. Thermogravimetric analysis (TGA) indicated a 25% weight loss in air at 450° C.

EXAMPLE II

[Aminoethyl(aminomethyl)]phenylethyltrimethoxysilane $H_2N(CH_2)_2H_2NCH_2$—Ph—$(CH_2)_2Si(OCH_3)_3$ A 5 L. 4 neck flask equipped with an overhead stirrer, addition funnel, water-cooled condensor and a thermometer was charged with 2 L. of di-isopropyl ether and 267 mls of anhydrous ethylene diamine. The contents were warmed to 40° C. and 275 g of (chloromethyl) phenylethyltrimethoxysilane (as prepared in step (a) of Example I) was added dropwise over two hours. The mixture was heated to reflux and stirred for an additional hour. It was then allowed to cool to ambient temperature.

A solution of one mole of sodium methoxide in 300 mls of methanol was prepared by adding 23 g of clean sodium to anhydrous methanol. The solution was added over one hour to the above stirred reaction mixture. A fine precipitate of sodium chloride formed. The mixture was filtered and distilled. Distillation yielded a 245 g fraction, b.p. 126°–30°/0.2 mm. The product was identified as the title product by IR and NMR, yield 82%.

A hydrolysate of the compound was prepared as described in Example I. TGA indicated a 25% weight loss in air at 435°.

EXAMPLE III (Aminomethyl) phenylethyldimethylmethoxysilane
$H_2NCH_2$—Ph—$(CH_2)_2Si(CH_3)_2OCH_3$ The method of this example is the same as Example I except that dimethylchlorosilane was substituted for trichlorosilane in step (a) and a 1:1 mole ratio of trimethylorthoformate was employed for step (b). The intermediates formed in steps (a) and (b) were:
(chloromethyl) phenylethyldimethylchlorosilane, b.p. 134°–5°/20 mm (92% yield)
(chloromethyl) phenylethyldimethylmethoxysilane, b.p. 135–7°/20 mm (98% yield)
The final product formed in step (c) was:
(aminomethyl) phenylethyldimethylmethoxysilane, b.p. 103°–112°/1 mm (41% yield)
TGA analysis of the title compound indicated a 25% weight loss at 430° C.

It should be noted that the amine functional group will generally be para or meta to the ethylene bridge on the phenyl ring, since mixed isomers of the vinyl benzylchloride starting material are used. In fact, about 40% of the amine functional groups will be para and about 60% meta to the ethylene bridge on the phenyl ring.

When the thermal stability of the novel compounds of the present invention, as demonstrated by thermogravimetric analysis (TGA), is compared with prior art amine functional silanes having gamma or aromatic substitution, it can be seen that the thermal stability is better than the gamma substituted silanes but not quite as good as the silanes wherein the phenyl group is directly bonded to the silicon atom. The following table compares the 25% TGA weight loss of the trialkoxysilane hydrolysates of Examples I and II with controls:

| functionality group on Si | $NH_2$ | $HNCH_2CH_2NH_2$ |
| --- | --- | --- |

| | functionality | NH$_2$ | HNCH$_2$CH$_2$NH$_2$ |
|---|---|---|---|
| (gamma) | CH$_2$CH$_2$CH$_2$ | — | 400° C. |
| | CH$_2$CH$_2$—Ph—CH$_2$ | 450° C. (Ex. I) | 435° C. (Ex. II) |
| (aromatic) | —Ph— | 470° C. | — |

The adhesion of a wide range of polymeric materials to siliceous fillers can be improved with the amine functional silanes of the present invention. Thus, higher thermal stability of the coupling agent has been found to correlate well with improved adhesion and improved mechanical properties of the polymer composites. Polymers for which favorable results are observed usually contain moieties that either react with the amine functional group or hydrogen bond with the amine nitrogen. Polyimide and polyurethane monomers and prepolymers would be expected to form covalent bonds to the silanes through the amines. Polyamides, polysulfones, polycarbonates, polyphenylene sulfides and polyesters would be expected to interact with the amine nitrogen.

The novel silanes of the present invention are particularly useful in connection with polymers which are processed at temperatures in excess of 350° C. and/or receive lengthy or continuous exposure to temperatures in excess of 150° C. Such polymers include polyamides, polysulfones, polyimides and polyphenylene sulfides. More particularly, the ethylene bridged aromatic amine functional silanes have demonstrated excellent utility in resins processed up to 400° C. and/or with continuous temperature exposure to 200° C. While the novel silanes of the invention may be used with lower temperature polymers as well, the economics of the production of these compounds is not as advantageous.

As will conventional silane coupling agents, the novel silanes of the present invention may be integrally blended with the mixture of polymer and siliceous filler, or may be applied directly to the siliceous filler prior to blending with the polymer. In the case of integral blending, the silane coupling agent should be present in an amount of about 0.025 to 1.5 percent by weight of the composite, and preferably about 0.1 to 0.2 percent by weight. Where the coupling agent is applied directly to the filler, such as glass fibers, the silane should be present in an amount of about 0.05 to 4.0 percent by weight of the filler.

Thermoplastic composites according to the present invention will now be illustrated in more detail with reference to the following specific, non-limiting examples:

EXAMPLES IV-IX

Water-sized chopped glass fibers (½" in length) were obtained from PPG Industries that were essentially free of polymeric binding agents, but contained 5–13% water. The high water content is essential for handling the fiberglass in the absence of polymeric binding agents. The water is removed during processing by exhausting feed sections of the extruder and vacuum venting the melt-mix. Water-sized type E glass fibers of K or M filament diameter were sprayed with a 5% solution of the silane in 95% denatured ethanol to yield 0.1% silane on the glass. Extrusions were made from low shear mixed blends of the treated glass and injection molding grade pellets. Extrusion temperatures were generally 10° C. above process temperatures recommended for unfilled resins. Extruded material was pelletized and molded into ASTM (D638) test specimens. In all cases reported for thermoplastic composites the glass content was 30±2% by weight of the composite. The silanes used to form the composites in the following examples were (aminomethyl) phenylethyltrimethoxysilane (prepared as in Example I), [aminoethyl(aminomethyl)]-phenylethyltrimethoxysilane (prepared as in Example II) and (aminoethyl) aminopropyltrimethoxysilane (used as a control and designated "a").

| Example | Silane | Resin Type | Resin Manufacturer | Tensile Strength (psi) |
|---|---|---|---|---|
| IV | I | polysulfone | Union Carbide | 19,200 |
| V | II | polysulfone | Union Carbide | 19,400 |
| control | a | polysulfone | Union Carbide | 18,600 |
| VI | I | polyamide-imide | Amoco | 28,200 |
| VII | II | polyamide-imide | Amoco | 29,700 |
| control | a | polyamide-imide | Amoco | 27,400 |
| VIII | II | nylon 6/6 | Monsanto | 27,900 |
| control | a | nylon 6/6 | Monsanto | 27,200 |
| IX | I | polyphenylene sulfide | Phillips | 20,500 |
| control | a | polyphenylene sulfide | Phillips | 18,400 |

The present invention may be embodied in other specific forms without departing from the spirit or essential attributes thereof and, accordingly, reference should be made to the appended claims, rather than to the foregoing specification as indicating the scope of the invention.

We claim:

1. An ethylene bridged benzylamine trifunctional silane of the formula:

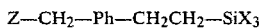

$$Z-CH_2-Ph-CH_2CH_2-SiX_3$$

wherein Ph is a phenyl group ($-C_6H_4-$), at least one X is a hydrolyzable group and Z is aminoethylamino.

2. A silane according to claim 1 wherein at least one X is displacable by hydrolysis during the reaction of the silane with a siliceous substrate and up to two X are nonhydrolyzable groups.

3. A silane according to claim 1 wherein at least one X is selected from the group consisting of alkoxy, alkoxy ether, acyloxy and amine, and the remainder of X are alkyl.

4. A silane according to claim 3 wherein at least one X is selected from the group consisting of methoxy, ethoxy and methoxyethoxy, and the remainder of X are selected from the group consisting of methyl and ethyl.

5. A silane according to claim 1 whose hydrolysate exhibits its 25% weight loss in air only at a temperature above 400° C. according to thermogravimetric analysis after dissolving the silane in water at a 5% concentration and drying the hydrolysate for four hours at 120° C.

6. [Aminoethyl(aminomethyl)]phenylethyltrimethoxysilane.

7. A method of making (aminomethyl) phenylethyldimethylmethoxysilane comprising the steps of:
(a) reacting dimethylchlorosilane with vinylbenzylchloride in the presence of a chloroplatinic acid catalyst, and distilling the reaction mixture to yield (chloromethyl) phenylethyldimethylchlorosilane;
(b) reacting said (chloromethyl) phenylethyldimethylchlorosilane with an equimolar amount of triethylorthoformate or methanol, and distilling the reaction mixture to yield (chloromethyl) phenylethyldimethylmethoxysilane; and
(c) reacting said (chloromethyl) phenylethyldimethylmethoxysilane with ammonia under heat and pressure, and distilling the reaction mixture to yield (aminomethyl) phenylethyldimethylmethoxysilane.

* * * * *